(12) United States Patent
Chamanzar et al.

(10) Patent No.: US 12,343,554 B2
(45) Date of Patent: Jul. 1, 2025

(54) IMPLANTABLE PHOTONIC PLATFORM

(71) Applicant: CARNEGIE MELLON UNIVERSITY, Pittsburgh, PA (US)

(72) Inventors: Maysamreza Chamanzar, Pittsburgh, PA (US); Jay W. Reddy, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 471 days.

(21) Appl. No.: 17/486,351

(22) Filed: Sep. 27, 2021

(65) Prior Publication Data

US 2022/0096860 A1 Mar. 31, 2022

Related U.S. Application Data

(60) Provisional application No. 63/084,133, filed on Sep. 28, 2020.

(51) Int. Cl.
*A61N 5/06* (2006.01)
*A61N 5/067* (2006.01)
*F21V 8/00* (2006.01)
*G02B 6/42* (2006.01)
*G03F 7/00* (2006.01)

(52) U.S. Cl.
CPC ......... *A61N 5/0601* (2013.01); *A61N 5/0622* (2013.01); *A61N 5/067* (2021.08); *G02B 6/0031* (2013.01); *G02B 6/4214* (2013.01); *G03F 7/0005* (2013.01); *A61N 2005/063* (2013.01); *A61N 2005/0643* (2013.01); *A61N 2005/0666* (2013.01)

(58) Field of Classification Search
CPC .... A61N 5/0601; A61N 5/067; A61N 5/0622; A61N 2005/063; A61N 2005/0643; A61N 2005/0666; G02B 6/0031; G02B 6/4214; G03F 7/0005
See application file for complete search history.

(56) References Cited

U.S. PATENT DOCUMENTS 9,062,960 B2 * 6/2015 Rubio Guivernau .. G02B 6/262
9,192,314 B2 * 11/2015 McLaughlin ............ A61B 5/24
9,261,350 B2 * 2/2016 Rubio Guivernau .... G02B 6/32
(Continued)

OTHER PUBLICATIONS

Reddy et al., Parylene photonics: a flexible, broadband optical waveguide platform with integrated micromirrors for biointerfaces. Microsyst Nanoeng 6, 85 (2020). https://doi.org/10.1038/s41378-020-00186-2 (Year: 2020).*

(Continued)

*Primary Examiner* — Peter Radkowski
(74) *Attorney, Agent, or Firm* — KDW FIRM PLLC

(57) ABSTRACT

Disclosed herein is a fully flexible photonic platform based on a high density, flexible array of ultra-compact optical waveguides composed of biocompatible polymers Parylene C and PDMS. The photonic platform features unique embedded input/output micro-mirrors that redirect light from the waveguides perpendicularly to the surface of the array for localized, patterned illumination in tissue. This architecture enables the design of a fully flexible, compact integrated photonic system to realize an implantable, wearable or on-chip photonic platform for application such as in vivo chronic optogenetic stimulation of brain activity.

19 Claims, 7 Drawing Sheets

(56) References Cited

U.S. PATENT DOCUMENTS

| | | | | |
|---|---|---|---|---|
| 9,486,641 B2* | 11/2016 | Tolosa | | A61N 5/0622 |
| 9,649,503 B2* | 5/2017 | Delp | | A61N 1/0551 |
| 9,662,508 B2* | 5/2017 | Delp | | A61P 9/12 |
| 9,690,093 B2* | 6/2017 | Margallo | | G01B 9/02051 |
| 9,700,736 B2* | 7/2017 | Seymour | | A61N 5/0622 |
| 9,814,900 B2* | 11/2017 | Lundmark | | A61P 9/12 |
| 9,821,170 B2* | 11/2017 | Lundmark | | A61N 5/0622 |
| 10,004,917 B2* | 6/2018 | Li | | A61N 5/0622 |
| 10,022,552 B2* | 7/2018 | Stahler | | A61B 17/00234 |
| 10,022,553 B2* | 7/2018 | Lundmark | | A61K 48/00 |
| 10,105,550 B2* | 10/2018 | Stahler | | A61K 48/00 |
| 10,188,870 B2* | 1/2019 | Lundmark | | A61P 9/12 |
| 10,213,617 B2* | 2/2019 | Lundmark | | A61N 5/062 |
| 10,232,583 B2* | 3/2019 | Clough | | G03F 7/0005 |
| 10,481,336 B2* | 11/2019 | Menard | | G02B 6/3518 |
| 10,512,787 B2* | 12/2019 | Delp | | A61K 38/164 |
| 11,125,948 B2* | 9/2021 | Menard | | G02B 6/357 |
| 11,169,326 B2* | 11/2021 | Huang | | G02B 6/4249 |
| 11,385,400 B2* | 7/2022 | Wheeler | | B05D 1/005 |
| 11,660,115 B2* | 5/2023 | Hanson | | A61B 5/688 |
| | | | | 600/378 |
| 11,860,415 B2* | 1/2024 | Huang | | G02B 6/4214 |
| 2002/0187350 A1* | 12/2002 | Saccomanno | | G02B 6/1221 |
| | | | | 428/458 |
| 2005/0008848 A1* | 1/2005 | Saccomanno | | G02B 6/1221 |
| | | | | 428/328 |
| 2006/0198569 A1* | 9/2006 | Ohtsu | | G02B 6/4246 |
| | | | | 385/14 |
| 2012/0287420 A1* | 11/2012 | McLaughlin | | A61B 5/24 |
| | | | | 356/72 |
| 2013/0030352 A1* | 1/2013 | Seymour | | A61B 5/24 |
| | | | | 604/20 |
| 2013/0046148 A1* | 2/2013 | Tathireddy | | A61N 5/0622 |
| | | | | 600/300 |
| 2013/0062457 A1* | 3/2013 | Deakin | | B64B 1/20 |
| | | | | 343/706 |
| 2013/0201485 A1* | 8/2013 | Rubio-Guivernau | | |
| | | | | G01B 9/02049 |
| | | | | 216/2 |
| 2014/0277296 A1* | 9/2014 | Tolosa | | A61N 5/0622 |
| | | | | 29/874 |
| 2015/0018901 A1* | 1/2015 | Li | | A61N 5/0622 |
| | | | | 607/92 |
| 2015/0202456 A1* | 7/2015 | Andersen | | A61K 38/177 |
| | | | | 604/20 |
| 2015/0246242 A1* | 9/2015 | Delp | | A61N 1/3605 |
| | | | | 604/20 |
| 2015/0247720 A1* | 9/2015 | Rubio Guivernau | | |
| | | | | G02B 6/1221 |
| | | | | 356/479 |
| 2015/0283397 A1* | 10/2015 | Andersen | | A61K 38/168 |
| | | | | 607/88 |
| 2015/0283398 A1* | 10/2015 | Andersen | | A61N 5/0601 |
| | | | | 607/88 |
| 2015/0360049 A1* | 12/2015 | Kaplitt | | A61K 48/00 |
| | | | | 607/88 |
| 2015/0360050 A1* | 12/2015 | Kaplitt | | A61N 5/062 |
| | | | | 607/88 |
| 2016/0030765 A1* | 2/2016 | Towne | | A61B 18/18 |
| | | | | 607/88 |
| 2016/0038755 A1* | 2/2016 | Lundmark | | A61K 38/16 |
| | | | | 607/92 |
| 2016/0038756 A1* | 2/2016 | Andersen | | A61B 17/00234 |
| | | | | 607/92 |
| 2016/0038757 A1* | 2/2016 | Stahler | | A61N 1/36053 |
| | | | | 607/92 |
| 2016/0038758 A1* | 2/2016 | Stahler | | A61K 41/00 |
| | | | | 607/92 |
| 2016/0038759 A1* | 2/2016 | Andersen | | A61N 5/062 |
| | | | | 607/88 |
| 2016/0038765 A1* | 2/2016 | Delp | | A61K 38/16 |
| | | | | 607/3 |
| 2016/0045764 A1* | 2/2016 | Delp | | A61B 17/3403 |
| | | | | 607/3 |
| 2016/0045765 A1* | 2/2016 | Lundmark | | A61M 25/0105 |
| | | | | 604/506 |
| 2016/0051828 A1* | 2/2016 | Stahler | | A61K 41/0057 |
| | | | | 607/88 |
| 2016/0051830 A1* | 2/2016 | Andersen | | A61K 48/0075 |
| | | | | 607/92 |
| 2016/0051831 A1* | 2/2016 | Lundmark | | A61K 38/177 |
| | | | | 604/95.01 |
| 2016/0051836 A1* | 2/2016 | Lundmark | | A61K 38/16 |
| | | | | 607/92 |
| 2016/0051837 A1* | 2/2016 | Delp | | A61K 38/164 |
| | | | | 607/92 |
| 2016/0051838 A1* | 2/2016 | Stahler | | A61N 1/3605 |
| | | | | 607/92 |
| 2016/0059030 A1* | 3/2016 | Huang | | A61N 1/36053 |
| | | | | 607/88 |
| 2016/0073887 A1* | 3/2016 | Lee | | H01B 11/22 |
| | | | | 600/377 |
| 2016/0082279 A1* | 3/2016 | Andersen | | A61K 48/0075 |
| | | | | 607/92 |
| 2016/0096034 A1* | 4/2016 | Lundmark | | A61K 38/164 |
| | | | | 607/92 |
| 2016/0096035 A1* | 4/2016 | Lundmark | | A61K 41/0057 |
| | | | | 607/92 |
| 2016/0109699 A1* | 4/2016 | Margallo Balbás | | |
| | | | | G01B 9/02091 |
| | | | | 359/205.1 |
| 2017/0057193 A1* | 3/2017 | Clough | | G02B 6/138 |
| 2017/0182191 A1* | 6/2017 | Towne | | A61K 48/0075 |
| 2017/0225008 A1* | 8/2017 | Stahler | | A61N 1/36053 |
| 2017/0225009 A1* | 8/2017 | Delp | | A61B 17/3403 |
| 2017/0225013 A1* | 8/2017 | Delp | | A61K 41/00 |
| 2017/0239488 A1* | 8/2017 | Stahler | | A61M 5/142 |
| 2018/0028832 A1* | 2/2018 | Lundmark | | A61K 38/177 |
| 2018/0056085 A1* | 3/2018 | Lundmark | | A61K 48/00 |
| 2018/0133501 A1* | 5/2018 | Stahler | | A61N 5/062 |
| 2018/0136389 A1* | 5/2018 | Wheeler | | G02B 6/262 |
| 2018/0140862 A1* | 5/2018 | Stahler | | A61K 41/0057 |
| 2018/0214711 A1* | 8/2018 | Stahler | | A61N 1/36053 |
| 2018/0280716 A1* | 10/2018 | Stahler | | A61M 5/20 |
| 2018/0296243 A1* | 10/2018 | Hanson | | A61B 5/0084 |
| 2018/0299622 A1* | 10/2018 | Menard | | G02B 6/3518 |
| 2018/0345033 A1* | 12/2018 | Lundmark | | A61K 41/00 |
| 2018/0361169 A1* | 12/2018 | Delp | | A61M 37/0015 |
| 2019/0015677 A1* | 1/2019 | Stahler | | A61M 5/20 |
| 2019/0038908 A1* | 2/2019 | Lundmark | | A61K 48/0075 |
| 2019/0099611 A1* | 4/2019 | Lundmark | | A61M 5/142 |
| 2019/0105507 A1* | 4/2019 | Stahler | | A61M 25/0147 |
| 2019/0117993 A1* | 4/2019 | Lundmark | | A61K 48/00 |
| 2019/0160300 A1* | 5/2019 | Delp | | A61K 48/00 |
| 2019/0224492 A1* | 7/2019 | Delp | | A61K 41/0057 |
| 2019/0240500 A1* | 8/2019 | Lundmark | | A61N 1/36053 |
| 2019/0265411 A1* | 8/2019 | Huang | | G02B 6/424 |
| 2019/0293838 A1* | 9/2019 | Haba | | G02B 27/0172 |
| 2019/0388700 A1* | 12/2019 | Delp | | A61M 25/0105 |
| 2020/0009397 A1* | 1/2020 | Lundmark | | A61K 38/168 |
| 2020/0049892 A1* | 2/2020 | Menard | | G02B 6/4214 |
| 2020/0114162 A1* | 4/2020 | Stahler | | A61M 37/0015 |
| 2020/0139151 A1* | 5/2020 | Lundmark | | A61M 25/0105 |
| 2020/0229704 A1* | 7/2020 | Lee | | G02B 6/4274 |
| 2022/0043209 A1* | 2/2022 | Huang | | G02B 6/13 |
| 2023/0371981 A1* | 11/2023 | Hanson | | A61N 5/0622 |

OTHER PUBLICATIONS

Edrei et al., The overwhelming role of ballistic photons in ultrasonically guided light through tissue. Nat Commun 13, 1873 (2022). https://doi.org/10.1038/s41467-022-29157-z (Year: 2022).*

Chamanzar et al. Ultrasonic sculpting of virtual optical waveguides in tissue. Nat Commun 10, 92 (2019). https://doi.org/10.1038/s41467-018-07856-w (Year: 2019).*

Kee et al., Design and fabrication of Poly(dimethylsiloxane) arrayed waveguide grating. Opt Express. Oct. 11, 2010; 18(21):21732-42. doi: 10.1364/OE.18.021732. PMID: 20941073. (Year: 2010).*

(56) References Cited

OTHER PUBLICATIONS

Reddy et al., Low-loss flexible Parylene photonic waveguides for optical implants, Opt. Lett. 43, 4112-4115 (2018) (Year: 2018).*

Zuo et al., Low loss, flexible single-mode polymer photonics, Opt. Express 27, 11152-11159 (2019) (Year: 2019).*

Scopelliti et al., Ultrasonically sculpted virtual relay lens for in situ microimaging. Light Sci Appl 8, 65 (2019). https://doi.org/10.1038/s41377-019-0173-7 (Year: 2019).*

Wiesmayr et al., A Polydimethylsiloxane (PDMS) Waveguide Sensor that Mimics a Neuromast to Measure Fluid Flow Velocity. Sensors (Basel). Feb. 22, 2019;19(4):925. doi: 10.3390/s19040925. PMID: 30813266; PMCID: PMC6412414. (Year: 2019).*

Prajzler et al., Flexible multimode polydimethyl-diphenylsiloxane optical planar waveguides. J Mater Sci: Mater Electron 29, 5878-5884 (2018). https://doi.org/10.1007/s10854-018-8560-z (Year: 2018).*

Libbrecht et al., Proximal and distal modulation of neural activity by spatially confined optogenetic activation with an integrated high-density optoelectrode. J Neurophysiol. Jul. 1, 2018;120(1):149-161. doi: 10.1152/jn.00888.2017. Epub Mar. 28, 2018. PMID: 29589813; PMCID: PMC6093952. (Year: 2018).*

Kuo et al., Novel flexible Parylene neural probe with 3D sheath structure for enhancing tissue integration, Lab Chip, 2013, 13, 554-561 (Year: 2013).*

Reddy et al., Parylene Photonic Waveguides with Integrated Vertical Input/Output Ports for Flexible, Biocompatible Photonics, 2019 20th International Conference on Solid-State Sensors, Actuators and Microsystems & Eurosensors, Jun. 2019, pp. 2448-2451, doi : 10.1109/TRANSDUCERS.2019.8808541. (Year: 2019).*

Reddy et al., High Density, Double-Sided, Flexible Optoelectronic Neural Probes With Embedded uLEDs. Front. Neurosci. 13:745. ( 2019) doi: 10.3389/fnins.2019.00745 (Year: 2019).*

Reddy et al., "Low-loss flexible Parylene photonic waveguides for optical implants", Optic Letters, vol. 43, No. 17, pp. 4112-4115, Sep. 1, 2018.

\* cited by examiner

IMPLANTABLE PHOTONIC PLATFORM

RELATED APPLICATIONS

This application claims the benefit of U.S. Provisional Patent Application No. 63/084,133, filed Sep. 28, 2020, the contents of which are incorporated herein in their entirety.

GOVERNMENT INTEREST

This invention was made with United States government support under CBET1512794 and ECCS1926804 awarded by the National Science Foundation and NS113303 awarded by the National Institutes of Health. The U.S. government has certain rights in the invention.

BACKGROUND

In biological sciences and clinical practice, optical methods for the imaging and manipulation of living tissue are preferred for noninvasive interaction. However, the scattering and absorption of light in tissue poses fundamental limitations to the achievable resolution and depth of penetration. Depending on the type of tissue and the wavelength of light, noninvasive optical microscopy techniques are typically limited to the superficial layers of tissue due to the scattering and absorption of light, especially in the visible range of the optical spectrum. Multi-photon techniques, which utilize simultaneous absorption of longer wavelength photons to activate visible-range optical agents, achieve deeper penetration into tissue due to reduced attenuation of near-infrared and infrared light. However, even when using advanced multiphoton techniques, optical access is still limited to a few millimeters deep into the tissue.

In the context of brain imaging and manipulation, accessing deeper regions is required to study the neural mechanisms of disorders, such as Parkinson's disease, that involve the malfunction of circuits in deep structures, namely, the basal ganglia nuclei. The issue of penetration depth is even more limiting for studying the large brains of non-human primates and humans.

Optical imaging and manipulation in free-roaming animal subjects requires miniaturized technologies that are much smaller than traditional bulky microscopes. Recently demonstrated miniaturized microscopes and mini-scopes, powered by electrical and fiber optic tethers, can be carried by a mouse during ambulatory experiments. Moreover, compact optical implants, such as light-emitting diodes, optical fibers, and integrated photonic waveguides, have been used to deliver or collect photons deep within tissues to record and stimulate disparate regions simultaneously. Unlike their external counterparts, these techniques require a physical device to be implanted into the tissue.

Among different biomedical applications, neurophotonics is an emerging field that demands minimally invasive and highly flexible optical implants for light delivery into the brain with high spatial resolution for optogenetic stimulation and functional imaging of brain activity. To study and understand the distributed and dynamic neural circuits in the brain, advanced methods are needed to monitor and manipulate neuronal activity at single-cell resolution over different areas of the brain during naturalistic behavior.

Brain tissue is especially vulnerable to damage from rigid implants. It has been shown that the performance of neural implants gradually degrades over time due to the foreign body response. This biological tissue response, which involves inflammation and astroglial scarring, is believed to be triggered, in part, by a mismatch between the mechanical properties of the implanted device and neural tissue. The buildup of scar tissue around the implantation site eventually degrades the recording signal-to-noise ratio and stimulation efficiency, thereby limiting the lifetime of such implants. For electrical recording, flexible polymer devices have been shown to reduce damage to the brain tissue and thus enable longer-term neural recording. An equivalent flexible optical platform is desired to enable chronic optical interrogation of neural circuits.

Most existing integrated photonic waveguides are made of rigid semiconductor materials and dielectrics such as silicon, silicon nitride, and silicon dioxide. These integrated photonic platforms are mainly designed for optical communications and are not necessarily optimized for implantable or wearable biophotonics. In addition to microfabricated integrated photonic devices, comparatively large single-channel light guides, including optical fibers and polymer silicone light guides, have been used for light delivery into tissue. Polymers such as SU-8 have also been incorporated into integrated photonic devices.

The overall stiffness of a device is determined by its geometry and Young's modulus. Therefore, in addition to the material properties, the foreign body response is also a function of the shape of the implanted device. Typically, implantable neural probes are fabricated in long, high-aspect-ratio shapes that minimize the cross-sectional area to reduce acute tissue damage during implantation. The probe mechanics in this shape are well characterized by the cantilever stiffness, which scales linearly with the Young's modulus of the material.

To advance scientific understanding of biological mechanisms and to aid clinical intervention, it would be desirable to provide compact, flexible devices which can be implanted to enable targeted light delivery deep into tissue, while also minimizing damage to the surrounding tissue due to the foreign body response.

SUMMARY OF THE INVENTION

Figure 1:
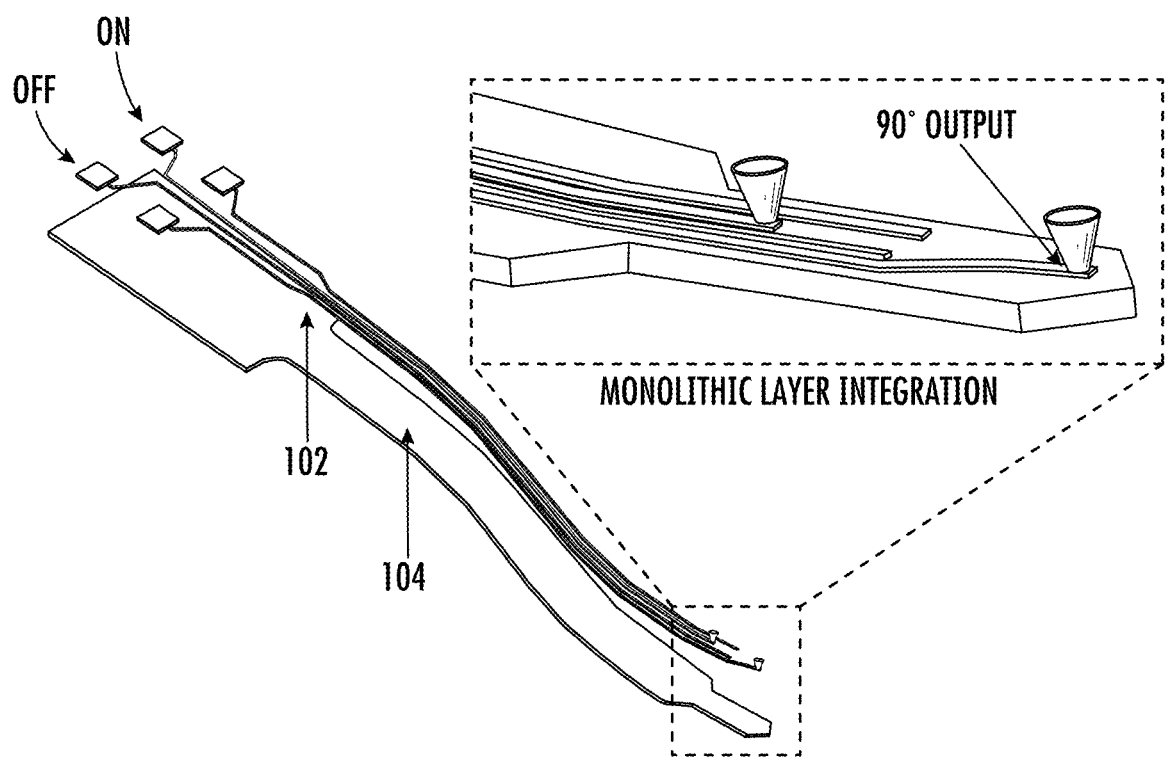
FIG. 1 is a schematic of the photonic platform disclosed herein, with an inset showing out-of-plane light delivery.

Compared with other commonly used materials for photonic waveguides, Parylene C and poly-dimethylsiloxane (PDMS) exhibit a Young's moduli closer to the values of most biological tissues, suggesting that this architecture will reduce the foreign body response and be less damaging to the surrounding tissue after implantation. Disclosed herein is an integrated photonic platform to realize a compact, biocompatible, and fully flexible polymer-based optical waveguide array that delivers light efficiently into tissue in a minimally invasive way.

The invention is realized entirely in a flexible, biocompatible material platform composed of Parylene C and PDMS polymers. PDMS is optically transparent in the visible range and is resistant to degradation from prolonged exposure to a biological environments. Both polymers are used in FDA-approved medical implants and are also widely used in research as well as clinical applications. With a proven history of biosafety in humans, Parylene C and PDMS form a compelling photonic platform for bio-interface development, with translational potential for medical applications.

The invention described herein comprises a fully flexible photonic platform supporting a waveguide made of biocompatible polymers, for example, PDMS and Parylene C. In some embodiments, a large refractive index contrast between these two polymers can enable the realization of very compact integrated photonic waveguides comprising Parylene C as the waveguide core and PDMS as the cladding. In some embodiments, the waveguides can be as small as one micron in cross-sectional dimensions. In some embodiments, the waveguides can be smaller than one micron in cross-sectional dimensions. In other embodiments, the waveguide cross-sectional dimension can be much larger, for example, on the order of tens or even hundreds of microns in a cross-sectional dimension, to form multimode waveguides. In some embodiments, the photonic waveguides can be flexible and can conform to the anatomical contours of the body. In some embodiments, the waveguides can exhibit a very small bend loss and remain very efficient in routing light through curved contours.

Other functional elements, such as Parylene photonic resonators, interferometers, filters and integrated mirrors can also be implemented in this platform to realize a fully functional integrated photonic system. Other than application in implantable neural probes, the invention described herein can include a Parylene photonic platform that can also be used to realize wearable photonic devices and optical interconnects for chip to chip or rack to rack interconnects in optical communications and processing.

DETAILED DESCRIPTION

Disclosed herein is a flexible photonic platform and a method of fabricating the platform. The flexible photonic platform, shown in schematic form in FIG. 1, utilizes a single waveguide or a dense array of waveguides in the shape of an implantable device to deliver light from external light sources deep into tissue. Light is coupled to each waveguide from light sources located at the back end of the device, which can remain outside of the tissue. In various embodiments, the light sources can be either integrated laser diodes or a fiber tether connected to an external laser source. The device, in one embodiment, has a long flexible shank that is implanted into the tissue to deliver light at the target depth. To minimize damage to the surrounding tissue, in one embodiment, the shank is designed to be very thin (~7 microns total thickness) and narrow (~60 microns waveguide pitch). The total shank width is determined by the number of waveguide channels and the size and pitch of waveguides. In various embodiments, the same material platform can support waveguides having a thickness and/or width in a range of less than 1 micron to 10 s of microns.

The waveguide core 102 is made of Parylene C, a biocompatible polymer having a high refractive index which is transparent throughout the visible range of the optical spectrum. PDMS 104 is used as the waveguide cladding due to its lower refractive index than that of Parylene C. The material choice of Parylene C and PDMS provides a large index contrast among biocompatible polymers to confine an optical mode. In other embodiments, it may be possible to substitute other optically-transparent polymers, as long as there is a refractive index contrast between the cladding and the waveguide core materials. A large index contrast improves mode confinement and results in a small bend loss. However, a large index contrast can also exacerbate the scattering losses due to sidewall roughness, which can be alleviated by smoothing the waveguide sidewalls by depositing a conformal layer of the material that comprises the core (Parylene C in a preferred embodiment) or another material with a close refractive index.

Figure 2:
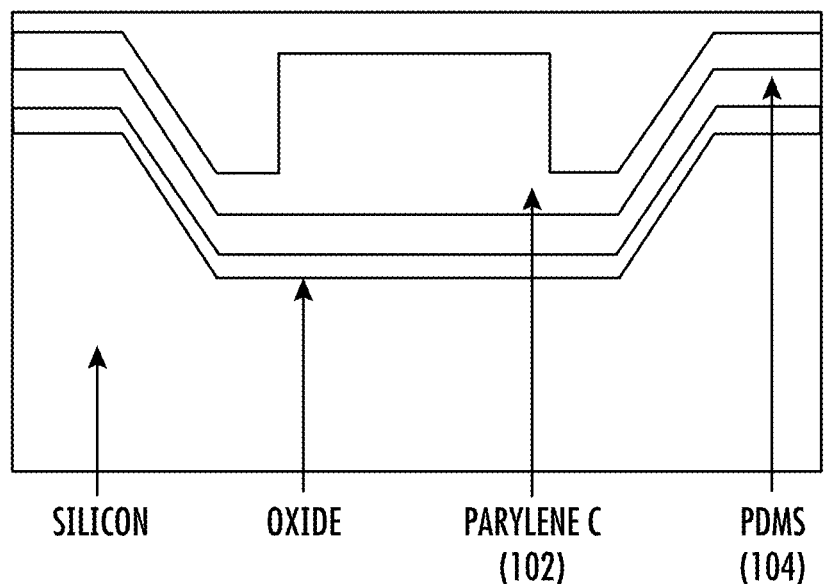
FIG. 2 is a schematic of a waveguide transverse cross-section depicted during fabrication on a silicon substrate.

A cross-sectional schematic of the waveguide structure on the wafer is shown in FIG. 2. This cross-sectional depiction shows the platform during the fabrication process, during which the substrate and oxide layers will be removed. The fabrication process is discussed later herein.

One novel feature of some embodiments of the invention is the monolithic integration of embedded micromirrors at the input and/or output ports, which enables broadband input/output coupling of light. In certain embodiments, the micromirrors are situated at a 45° angle with respect to a longitudinal axis of the waveguide, such as to direct the light transmitted by the waveguide in a direction perpendicular to the longitudinal axis of the waveguide. The inset portion of FIG. 1 shows the light cones being emitted in a direction perpendicular to the longitudinal axis of waveguide by the action of the micromirrors. In various embodiments, the micromirrors may be positioned at other angles with respect to the longitudinal axis of the waveguide. In various embodiments, micromirrors may be fitted at the input port, the output port, or both the input and output ports of one or more of the waveguides. In some embodiments, the micromirrors may be excluded.

Figure 3:
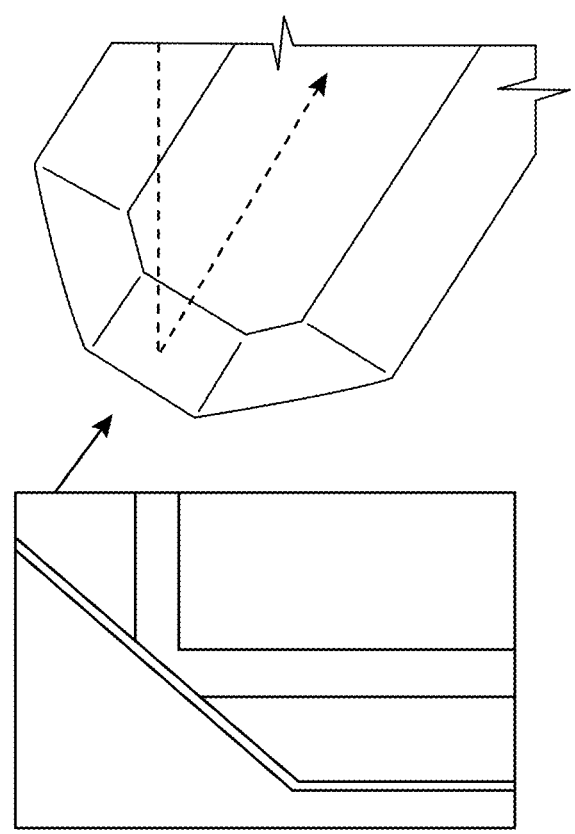
FIG. 3 is a scanning electron microscope (SEM) image of a trench etched in a substrate with the {1 1 0} plane indicated, which acts as the mold for the micromirror at the input or output ports, as shown in the cross-sectional portion of the figure.

The mirror topography is first precisely defined in a mold, as shown in FIG. 3, and then transferred to the flexible polymer device via deposition of Parylene C and PDMS onto the mold. In preferred embodiments, the mold is composed of silicon, but other material may also be used. In some embodiments, a negative mold may be used, wherein the shape is embossed on the substrate material using soft lithography. In some embodiments, the mold shape may be lithographically defined in a photo-definable polymer.

Figure 4:
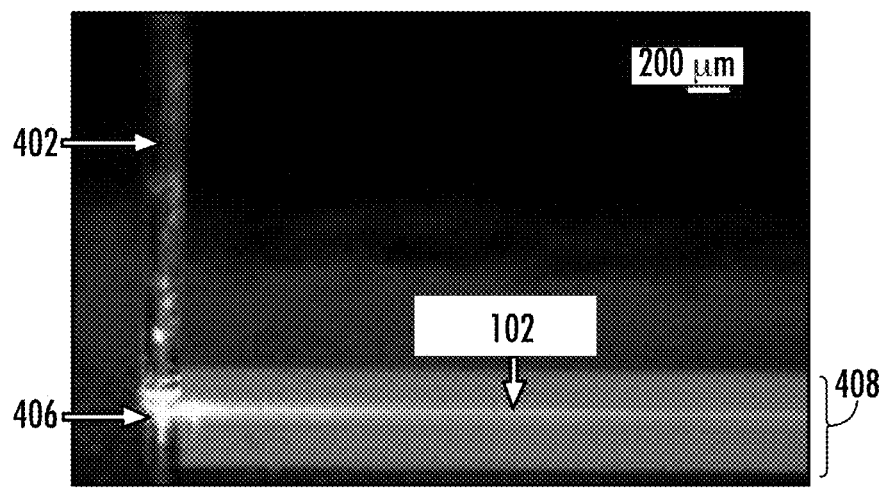
FIG. 4 shows out-of-plane light coupling from an optical fiber to the Parylene C waveguide using a 45° micromirror at the input port.

The monolithically embedded micromirror structures are capable of providing 90° out-of-plane input/output light coupling between the light source and the waveguide, as shown in FIG. 4, which shows out-of-plane light coupling from an optical fiber 402 to one of the Parylene C waveguides 404 in waveguide array 408 using a 45° micromirror at the input port 406.

Figure 5:
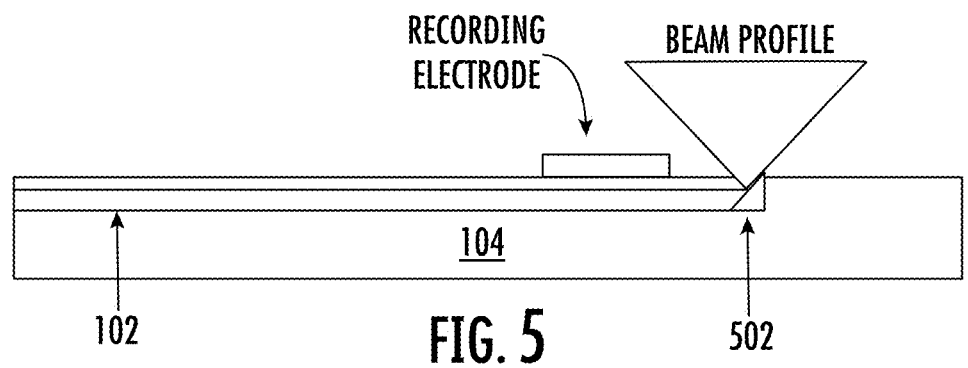
FIG. 5 is a schematic diagram showing the output port of the waveguide illustrating out-of-plane illumination, where the waveguide illumination is oriented perpendicular to the surface of the waveguide.

A micromirror used as an output port 502 is shown in FIG. 5. When used as an output port 502, the micromirrors enable out-of-plane illumination normal to the surface of the implantable device. Traditional optical waveguides and fibers operate in an end-firing configuration in which light is emitted from the end facet of the waveguide. End-firing waveguides result in an in-plane optical beam profile that is oriented along the longitudinal axis of the probe, causing a large portion of the probe surface area to be illuminated and limiting the number of non-overlapping output ports that can be arranged on the surface. To enable a high spatial resolution illumination pattern along the probe shank, an out-of-plane scheme is preferred, as shown in FIG. 5. In addition, in the context of neural probes, where electrical recording sites are also patterned on the surface of the shank, an out-of-plane beam profile avoids direct illumination of recording electrode sites, reducing the severity of photoelectric artifacts. Out-of-plane beam profiles are useful to co-locate stimulation with surface electrode arrays on the same probe shank Output ports 502 may be lithographically defined in any desired arrangement along the probe shank 104 to suit the purpose of the intended experiment. Although the photonic platform can be broadly used in any biomedical application, the invention is explained herein in the context of neural stimulation using optogenetics. For example, output ports may be spaced along the length of the shank 102 of the device to stimulate different regions of tissue (e.g., different layers of the cortex) or placed in a dense grid for interrogation of neural circuits in the same region.

Figure 6:
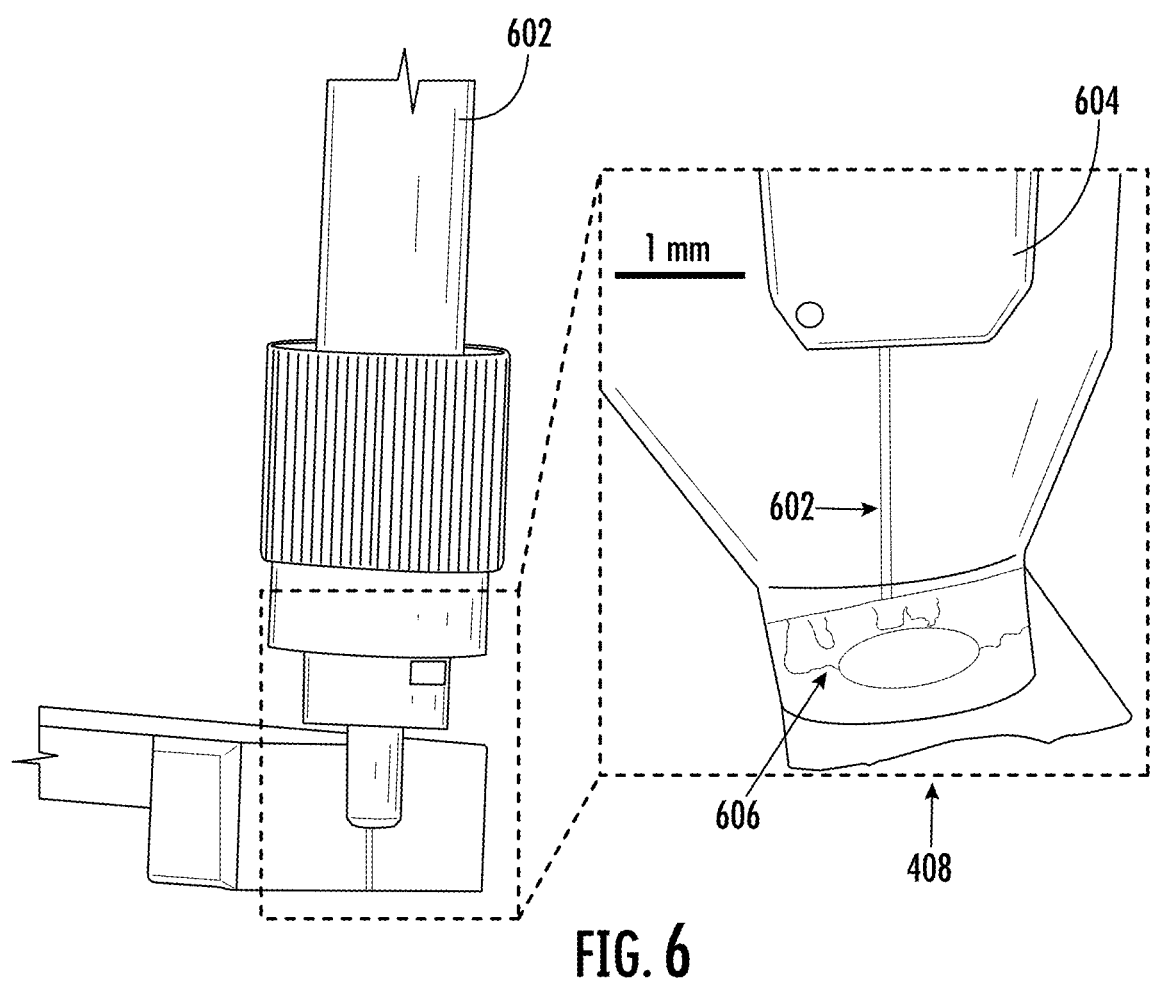
FIG. 6 shows the bonding of a light source to the input port of a waveguide.
Figure 7A:
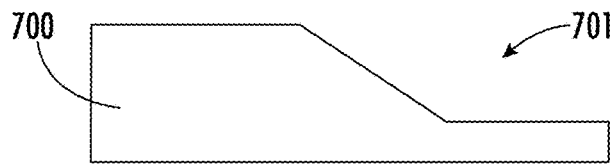
FIG. 7 schematically shows steps (a)-(g) in the fabrication of the photonic platform.
Figure 7B:
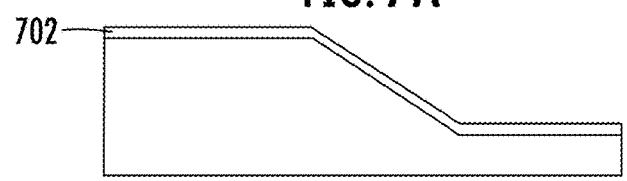
Figure 7C:
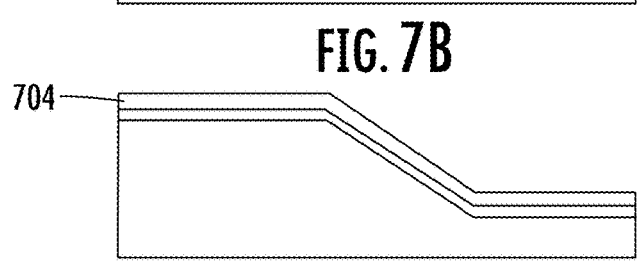
Figure 7D:
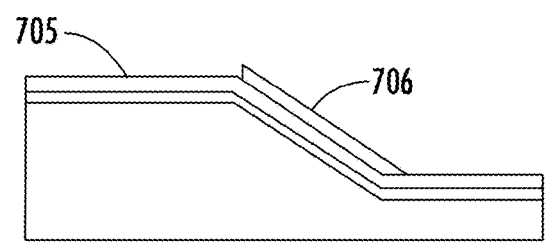
Figure 7E:
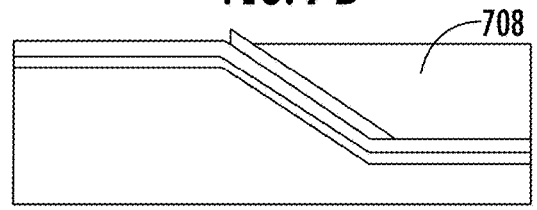
Figure 7F:
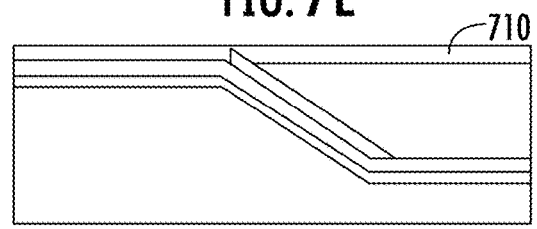
Figure 7G:
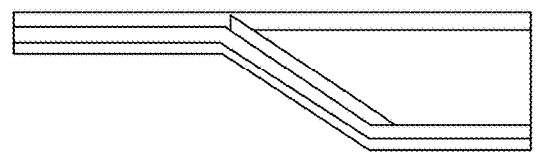

The packaging of microfabricated optical waveguides with light sources is required for implantable applications. The device backend must be compact and robust to enable implantation. The embedded micromirror input ports facilitate coupling of light from the surface into the integrated photonic waveguides. Optical fibers 602 can be aligned to the waveguide input facet using a 3D printed V-groove 604, illustrated in FIG. 6 and directly bonded to the waveguide array 408 with optical epoxy 606, as shown in the inset of FIG. 6. Due to the compact size of the optical fibers (3.0 µm core diameter, 125 µm cladding diameter), many fibers may be bonded to the probe backend, allowing independent light coupling to multiple waveguides in the array. The optical fiber operates as a single-mode fiber over wavelengths of 400-680 nm, covering the entire visible spectrum, which is relevant for most optical reporters and commonly used opsins for optogenetic stimulation. Packaging optical fibers at the backend of the implantable optical waveguide arrays has the advantage of enabling operation at different wavelengths using different external laser sources. In other embodiments, other sizes of optical fibers, other designs and constructions of alignment jigs, including machined pieces, or other types of optical epoxy may be used.

It is highly desired that implantable photonic waveguide probes are realized such that the prohibitive tether connections to the backend are either eliminated or at least reduced in size to enable chronic experiments on free-roaming animals. Utilizing the micromirrors for input coupling, compact vertical-cavity surface-emitting laser (VCSEL) chips may be directly bonded to the input facet using a thin layer of anisotropic conductive film (ACF). In one embodiment, the diode chips may emit at a wavelength of 680 nm and are both compact and lightweight. The ACF provides mechanical and electrical connections to the VCSELs without significantly attenuating the light. Using the present invention, an optical transmission of more than 67% through the ACF across the visible range of optical wavelengths can be achieved. Direct integration of light sources obviates the need for an external fiber-coupled laser source. Thus, the photonic platform described herein requires only an external electrical connection to a pair of small wires, which can be much less cumbersome and restrictive than a brittle, delicate fiber connection. Other than ACF, other thin film adhesives can also be used as long as the electrical connection is made through the bondpads using for example, gold bonding.

Fabrication Process

A method of fabricating the photonic waveguide of the present invention will now be disclosed. The process is schematically illustrated in steps (a)-(g) shown in FIG. 7. Parameters used in each step of a preferred embodiment of the fabrication process are shown in Table 1 below. As would be realized by one of skill in the art, many other fabrication processes, using different processing steps, materials or parameters, may be used to obtain similar results.

Figure 8:
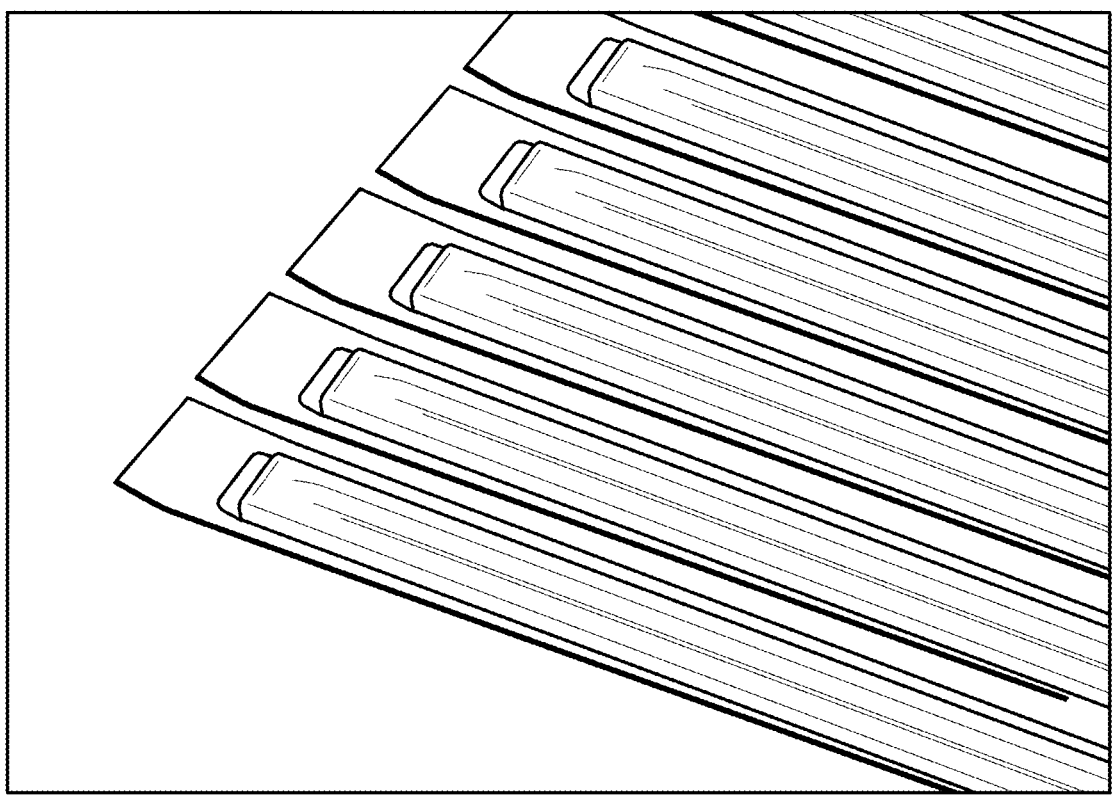
FIG. 8 is a SEM image of a substrate having multiple trenches defined therein for placement of a plurality of waveguides.

Preparing the Mold—The Parylene C photonic waveguides and integrated micromirrors disclosed herein may be fabricated on a silicon wafer (n {1 0 0}) with a 1 micron thermal oxide coating. In other embodiments, the mold can be formed in materials other than silicon. The thermal oxide layer serves as a hardmask for the etching of one or more trenches in the silicon. In some embodiments, other materials may be used for the hardmask. In some embodiments, multiple trenches may be etched, as shown in FIG. 8, while, in other embodiments, a single, wider trench may be defined in the substrate. In some embodiments, a negative mold may be used, wherein the shape is embossed on the substrate material using soft lithography. In some embodiments, the mold shape may be lithographically defined in a photo-definable polymer.

The thermal oxide layer is patterned using optical lithography and anisotropic reactive ion etching (RIE) using the parameters shown in process step 1 in Table 1. Then, in one embodiment, 45° trench sidewalls were formed using wet etching in potassium hydroxide (KOH) mixed with Triton X-100 surfactant, using the parameters shown in process step 2 in Table 1, to reach the desired trench depth. In other embodiments, different chemicals and surfactants, such as TMAH and IPA, may be used to etch the mold. In one embodiment, the desired trench depth is approximately of 6 microns. The oxide hardmask was subsequently stripped via wet etching in 49% HF. Careful design of the mask orientation with features at 45° to the {1 0 0} plane, indicated by the wafer main flat, is required to expose the {1 1 0} crystal plane and define the micromirror surface 302, shown in FIG. 3. The patterned Si surface serves as a mold for subsequent polymer layers, defining the 3D shape of the micromirrors. The silicon wafer 700 having the trench 701 defined therein is shown in step (a) of FIG. 7. Note that FIG. 7 shows only a portion of a side cross-sectional view of one of the one or more trenches defined on the silicon wafer.

Subsequently, a conformal oxide layer 702, shown in step (b) of FIG. 7, was deposited on the patterned Si surface using a plasma-enhanced chemical vapor deposition (PECVD) process, using the parameters shown in step 3 in Table 1. The conformal oxide layer 702 acts as a sacrificial layer to enable device release from the Si mold, as described later herein. In some embodiments of the invention, conformal oxide layer 702 is approximately 300 nm in thickness. In some embodiments of the invention, other conformal thin films can be used as the sacrificial layer.

Spin-Coating the PDMS Substrate—To form the substrate for the waveguide structure, a 1 micron PDMS layer 704 is spin-coated on the silicon mold, over the conformal oxide layer 702, as shown in step (c) of FIG. 7. Due to the high viscosity of PDMS, a layer of this relative thinness requires dilution with hexane prior to spin-coating. In various embodiments, the PDMS was diluted in a 1:10 ratio of PDMS:hexane by volume, thoroughly mixed, and filtered through a 0.2 micron membrane filter to remove any particulates. The solution is then spin-coated for 60 s at 2000 rpm and then degassed in a 400 mTorr vacuum for 4 min. Finally, the wafers are oven-baked for approximately 45 min at 100° C. to cure the thin film and remove the solvent. The PDMS spin-coating process is not perfectly conformal and is affected by the waveguide trench topography. The spin-coating parameters and size of the trench must be optimized to achieve the desired thickness at the bottom of the trench. Other methods of coating PDMS such as spray coating or chemical vapor deposition may be used. In other embodiments, different methods for coating the cladding layer including spray coating and PECVD, CVD, iCVD, or oCVD processes may be used. Multiple waveguides can be routed through a wide common trench.

Metal Micromirrors—Due to the low surface energy of PDMS, photoresistcannot be directly spin-coated onto its surface for lithography. To overcome this issue, the fabrication process includes the deposition of a very thin layer of Parylene C film 705, as shown in step (d) of FIG. 7, onto the PDMS layer 704 to serve as an adhesion layer for the photoresist and to enable optical lithography. In preferred embodiments, the Parylene C film 705 is ~300 nm in thickness. The parameters of this deposition are shown in step 4 of Table 1. The direct chemical vapor deposition (CVD) of Parylene C on PDMS provides strong adhesion, making Parylene C an ideal material. In other embodiments, the surface of PDMS may be prepared for lithography by coating a different thickness of Parylene C, by coating another adhesion layer, or by directly functionalizing the surface of PDMS by, for example, using oxygen plasma.

Embedded metal micromirrors 706 were then patterned using a lift-off process consisting of lithography and evaporation of 5 nm Pt and 100 nm Al films. The parameters for this step are shown in steps 5 and 6 of Table 1. Pt serves as a strong adhesion layer to Parylene C, while Al is used as the surface of micromirror 706 for its high reflectance across the visible spectrum. Lift-off was performed via acetone soaking, followed by pulsed sonication. The root mean square surface roughness of the Al micromirrors 706 is approximately 49.3 nm with a standard deviation of 3.7 nm from mirror to mirror. In other embodiments, alternative metals and layer thicknesses may be used. In other embodiments, the deposition process may be optimized to reduce the metal surface roughness.

Waveguide Core Etching and Smoothing—In the next step of the fabrication process, the waveguide core was realized in a subsequent layer of Parylene C. Parylene C is deposited to a thickness of approximately 3.5 microns using the CVD process described earlier. To define the outlines of individual waveguides, Parylene C was removed from the surrounding regions using an anisotropic oxygen plasma etching process. A 40 nm sputtered chromium (Cr) hard mask was used to achieve a high selectivity for etching Parylene C. The parameters of this step are shown in step 7 of Table 1. The waveguide patterns were aligned to the mirrors using a contact lithography process and the hard mask was patterned by wet etching of Cr. In other embodiments, different mask materials, such as Al or photoresist, may be used. In other embodiments, different mask thicknesses may be used to etch Parylene C, depending on the desired height of the waveguide.

The patterns were then transferred to Parylene C via oxygen plasma RIE using the parameters shown in step 8 of Table 1. PDMS acts as an etch stop layer because it is not effectively etched by oxygen plasma alone. After the Parylene C was etched, the Cr hardmask was stripped with Cr etchant.

The etched sidewall roughness results in optical scattering and significant propagation loss, thus rendering the optical waveguide impractical for the efficient guiding of light. To address this issue, an additional conformal layer of Parylene C is deposited over the etched sidewalls to reduce the sidewall roughness and the associated propagation loss. In preferred embodiments, the conformal layer of Parylene C is approximately 1.3 microns in thickness. This technique is used to smoothen the etched sidewalls and reduce the propagation loss of the waveguides. The three sequential Parylene C layers, (i.e., the thin layer on the PDMS substrate 705, the waveguide layer 708, and the conformal coating on the top, form the waveguide core which, in preferred embodiments, has a total thickness of approximately 5 microns. The result is shown in step (e) of FIG. 7, showing one of the waveguides. An upper cladding layer of PDMS 710, shown in step (f) of FIG. 7 is then added by spin coating. In other embodiments, the sidewall may not be smoothed.

Device Release—An Al hardmask is then sputtered to define the outline of the entire waveguide array using the parameters in step 9 of Table 1. The Al hardmask, in preferred embodiments, is approximately 1 micron in thickness and is lithographically patterned and wet etched. The PDMS cladding 710 is etched, and arrays were singulated using RIE, using the parameters in step 10 of Table 1. The Al hardmask is then stripped. To release the device, the silicon substrate 700 is first thinned down to 100 microns using backside etching in $SF_6$, using the parameters in step 11 of Table 1, and then the thinned Si wafer is completely etched in a subsequent etching step in $XeF_2$. The sacrificial oxide layer serves to protect the backside of the waveguide array. Once the Si layer 700 was removed, the sacrificial layer 702 is stripped in buffered HF acid, resulting in a released, flexible waveguide array, shown in step (g) of FIG. 7. The device is then thoroughly rinsed in deionized water after release to avoid contamination of biological tissues by the process chemicals. In other embodiments, a mask of a different material or thickness may be used. Other methods such as backside grinding can also be used to thin down the silicon layer or remove it.

Optical Fiber Bonding—A drop of optical quality epoxy is first placed on the waveguide array backend. An optical fiber is then fixed to a custom-designed 3D printed fixture with a V-groove, illustrated in FIG. 6, and aligned to the input micromirror using a precision micromanipulator. After maximizing the input coupling efficiency, the epoxy is thermally cured using the parameters in step 12 in Table 1, to provide a stable mechanical connection between the fiber and the waveguide array. In other embodiments, UV-cured, or self-curing epoxy may be used.

VCSEL Light Source Bonding—ACF film is first placed over the input micromirror. The VCSEL chip is then aligned to the input facet using a commercial flip-chip bonding tool. Once aligned, the ACF was cured, using the parameters in step 13 of Table 1, to fix the VCSEL chip in place. The p-contact and n-contact of the diode are electrically connected to an external PCB using an Al wirebond.

Figure 9:
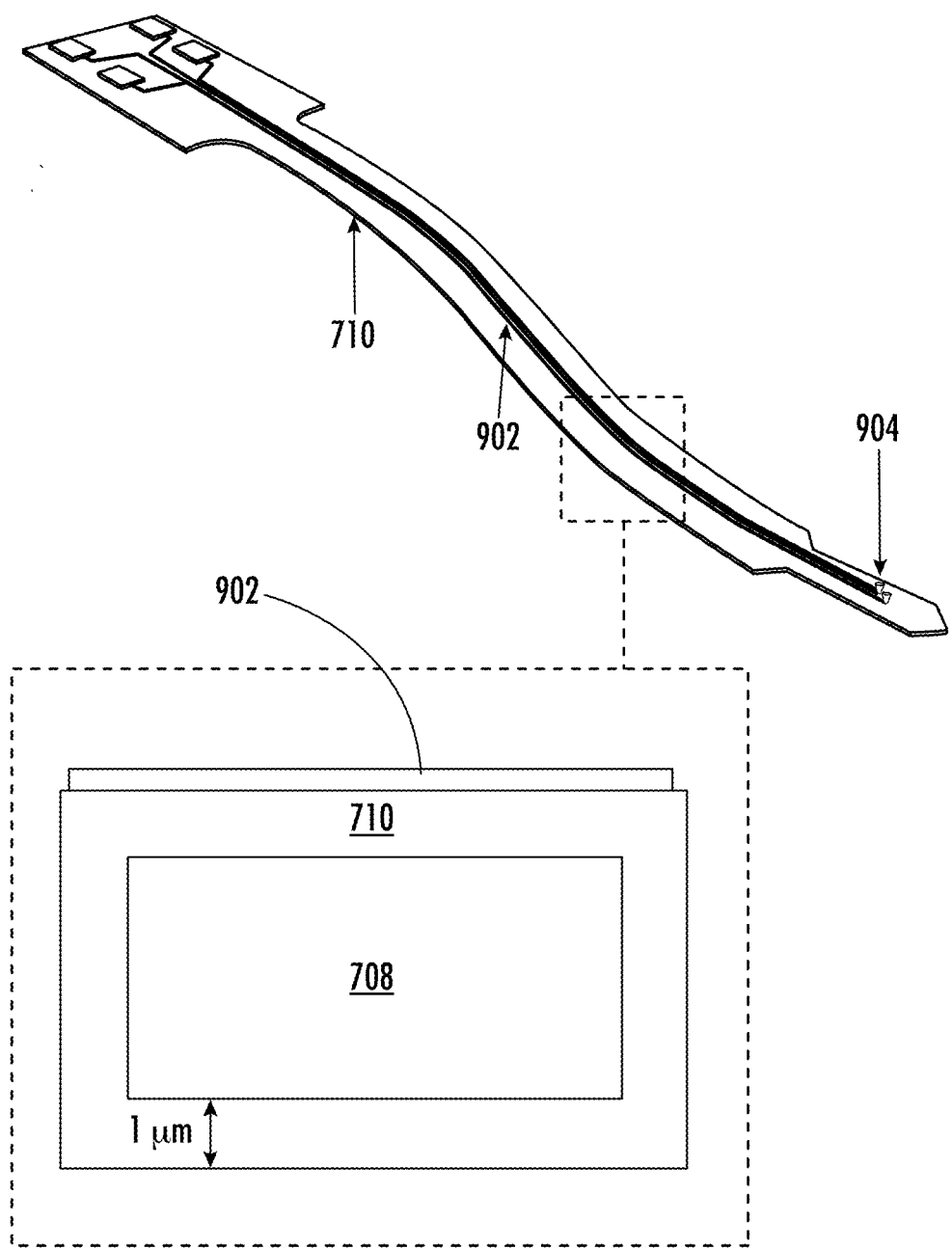
FIG. 9 shows an additional embodiment wherein electrical traces are placed on the surface of the photonic platform.

In the context of neural interfaces, both electrical recording and optical stimulation capabilities are desired to enable simultaneous electrophysiology recording and optogenetic stimulation experiments in the brain. Recording electrodes are usually formed via exposed metal sites connected by traces embedded in polymer insulation. A conceptual schematic diagram of an additional planar layer of recording electrodes 904 on a Parylene photonic waveguide is shown in FIG. 9.

One concern of combining electrical and optical functionalities on the same platform is the interaction of the optical waveguide modes with electrical traces, which will decrease the delivered optical power due to absorption losses in the metal. Commonly used metals such as Au, Pt, Ti, and Al exhibit large absorption coefficients in the visible range of the optical spectrum. In the device architecture disclosed herein, electrical traces 902 can be routed along the length of the device, parallel to the optical waveguides. Therefore, any significant interaction between the guided optical mode and metal traces 902 would cause significant attenuation of light after traversing the full length of the device. This interaction can be minimized by routing the electrical traces 902 through a separate layer, vertically spaced from the photonic layer 708 by the PDMS cladding 710, as shown in FIG. 9. A recording electrode 904 may be bonded to the electrical trace 902 at the distal end of the photonic platform.

TABLE 1

Process Parameters

| Process Step | Parameters | Rate |
|---|---|---|
| (1) Thermal Oxide Etch | Pressure: 100 mTorr<br>Gas: 22.5 SCCM<br>Gas: 16 SCCM $O_2$<br>Power 200 W | 55 nm/min |
| (2) Anisotropic Si Etch | Concentration: 2M KOH<br>Concentration: 60 ppm Triton X-100 Surfactant<br>Temp: 90° C.<br>Agitation: 210 RMP stirring | 280 nm/min |
| (3) PECV Oxide Deposition | Temp: 375° C.<br>Pressure: 900 mTorr<br>Gas: 75 SCCM $N_2O$<br>Gas: 70 SCCM $SiH_4$ | 60 nm/min |
| (4) Parylene Deposition | Furnace Temp: 690° C.<br>Chamber Gauge Temp: 135° C.<br>Vaporizor Temp: 175° C.<br>Pressure: 35 mTorr | 2 g → 1.47 μm |
| (5) Pt Evaporation | Pressure: $3 \times 10^{-7}$ Torr | 3 Å/s |
| (6) Al Evaporation | Pressure: $3 \times 10^{-7}$ Torr | 5 Å/s |
| (7) Cr Sputtering | Pressure: 7 mTorr<br>Gas: 50 SCCM Ar<br>Power: 50 W RF | 10 nm/min |
| (8) Parylene Etching | Gas: 14.0 SCCM $O_2$<br>Pressure: 50 mTorr<br>Power: 50 W RF | 250 nm/min |
| (9) Al Sputtering | Power: 100 W RF<br>Pressure: 5 mTorr | 30 nm/min |
| (10) PDMS Etching | Pressure: 75 mTorr<br>Gas: 30 SCCM $CF_4$<br>Gas: 10 SSCM $O_2$<br>Power: 200 W | 200 nm/min |
| (11) Si Etching | Pressure: 25 mTorr<br>Gas: 30 SCCM $SF_6$<br>Power: 100 W | 2.3 μm/min |
| (12) Epoxy Curing | Temp: 60° C.<br>Time: 2 hr. | |
| (13) ACF Curing | Temp: 120° C.<br>Time: 15 miin | |

The Parylene photonics platform operates over a wide range of wavelengths, especially in the visible range, relevant for optogenetic stimulation of neural activity. The input/output mirrors are broadband and enable coupling of light at different wavelengths. The propagation losses of the Parylene C waveguides disclosed herein are comparable with prior art SiN waveguides used in neural probes. The specific propagation loss of a microfabricated waveguide depends on its geometry and material properties as well as the fabrication process optimization. The primary source of optical loss in the Parylene C waveguides is the waveguide sidewall roughness resulting from etching the outline of the waveguide core. The Parylene photonic waveguides disclosed herein exhibit low losses over a wide range of the spectrum, including 450-680 nm, and the input-output coupling is broadband, Therefore, Parylene photonics can operate over a wide range of wavelengths.

The Parylene photonics platform is designed as a flexible photonic architecture that can freely flex with the tissue to avoid exerting strain on the tissue. To operate reliably in vivo, the bends induced by tissue motion should not significantly impact the delivered optical power at the output port. However, bending of optical waveguides typically results in radiation of confined optical modes before light reaches the output facet. The photonic platform disclosed herein exhibited negligible bend losses for millimeter-scale bends (i.e., more than 95% of the maximum output intensity even at a bend radius of 1.5 mm). Overall, empirical data suggests that the flexible waveguides disclosed herein preserve their performance through millimeter-scale bends in the probe shank. Bends of this size (i.e., 1.5 mm-5 mm) are likely to occur during implantation and routing of the flexible shank in the body. The empirical data suggests that the output optical power will be minimally affected by flexing in the tissue after implantation.

In addition to enabling broadband vertical input coupling, the 45° output micromirrors are capable of localized broadband illumination normal to the surface of the photonic platform. The output beam profile reflected by the micromirror was quantitatively measured to have a beam width of 13° orthogonal to the surface of the probe. In other embodiments, the output beam divergence may be a different angle. This allows for multiple output ports to be independently spaced along the probe surface for targeted light delivery.

The embedded micromirror input/output port is a versatile feature of the photonic platform disclosed herein. The micromirrors are broadband, unlike traditional out-of-plane illumination mechanisms such as grating couplers, which are highly wavelength dependent. Using the micromirrors, light at multiple wavelengths can be coupled to the waveguides. In the context of neural probes, different optogenetic wavelengths can be used to switch between stimulation and inhibition or to perform cell-type specific targeting. The Parylene photonics platform disclosed herein is the first to enable such high-resolution, broadband, out-of-plane light delivery in a fully compliant and biocompatible platform. The waveguide output power can be controlled by changing the input optical power. Off-target illumination is minimal because the extinction between the output port light intensity and the outscattered background light from the probe shank near the output port is minimal. If the input power is very high, outscattered light along the probe shank can be further reduced by using additional optical shielding layers. For biological experiments, the input power must be carefully chosen to achieve an output power that is higher than the threshold of activation or detection of the optical agent of interest, while also remaining lower than the threshold of photothermal damage to the tissue at the wavelength of operation.

The Parylene photonics platform disclosed herein utilizes flexible polymer materials to reduce the foreign body response after implantation. However, the overall device stiffness depends on the shape of the probe cross-section in addition to the material platform. For example, wide and thin probes are highly compliant when bent along the probe length but have higher stiffness along the width of the probe, resulting in a greater foreign body response along the probe edges. Therefore, a neural probe design with a compact footprint (i.e., thin and narrow), in addition to a soft material platform, is necessary to minimize damage to the tissue. The number and size of optical channels must be chosen such that the overall width of the probe is minimized.

The refractive index contrast between Parylene C and PDMS is sufficiently large to realize ultra-compact optical waveguides that have well-confined modes even for small cross-sectional dimensions of 1×1 microns. At this small size, the mode exposure to the sidewall is increased, which necessitates process optimization to fabricate such devices with smooth sidewalls and reduce scattering losses. In a dense array configuration, the waveguides exhibit negligible crosstalk of less than 30 dB over 5 cm length. This suggests that, under ideal conditions, the photonics platform can be scaled to realize waveguide arrays even with an extremely dense pitch of 2 microns Another factor that limits the size and density of a multichannel device is the light source coupling at the device input. Herein is disclosed the bonding of a single fiber to the waveguide input facet. Although the fiber core and cladding are small (i.e., 125 micron diameter), serial bonding of individual fibers must take into account the prohibitive size of the fiber ferrule and its sleeve, which is typically 2.5 mm. Scaling the bonding process to many channels requires matching the waveguide spacing to the pitch of commercially available photonic chip coupler arrays, which are now available at channel pitches in the range of 20-127 microns.

In addition to coupling light from benchtop laser sources with a fiber tether, the versatility of the embedded micromirror input ports can be leveraged for direct out-of-plane coupling of light to the polymer waveguides from laser diode chips. The low weight of the VCSEL sources is important in the context of chronic experiments on freely moving subjects, where the weight budget is typically 10% of the weight of the animal. An integrated laser diode platform may be directly powered and modulated via electrical power supplies integrated into a headstage or used for tetherless experiments with the addition of a battery and a radio frequency (RF) module. Due to the relatively large output facet of the bare chip VCSEL sources used herein, a large input port is required to achieve efficient coupling into the waveguide. In other embodiments, the waveguide can be tapered to achieve high coupling efficiency while routing compact waveguides in the probe shank, or more compact laser diodes can be used.

The fabrication process outlined in this paper to realize Parylene photonics is compatible with commonly used microfabrication techniques, During the fabrication process, harsh chemicals such as hydrofluoric (HF) acid are employed as an efficient way to remove the oxide hardmask and sacrificial layers, necessitating careful rinsing indeionized water to avoid tissue contamination. Other hardmask and sacrificial release layers, such as germanium, which can be removed using biosafe solvents (e.g., 1% hydrogen peroxide), could be used as alternatives. The scalable microfabrication process enables monolithic integration of additional planar structures prior to release. Thus, using this platform, additional photonic layers can be stacked to increase device density, or electrical layers can be added to create a multimodal flexible device platform.

The Parylene photonic platform disclosed herein shows great promise for realizing flexible chronic implantable biointerfaces, including neural probes, which can reduce the foreign body response in tissue. The out-of-plane, broadband input/output ports enabled by embedded micromirrors allow the devices to create patterns of localized illumination beams normal to the surface for collocated integration with recording electrodes and enable direct packaging with light sources on the probe backend. This photonic device platform is broadband and offers unprecedented flexibility in choosing the desired wavelength of light for opsins and optical reporters.

As would be realized by one of skill in the art, many variations in the design of the device and in the fabrication process are possible and are contemplated to be within the scope of the invention. For example, the photonic platform may be designed with waveguides of varying depths or widths, or with a varying number of waveguides defined on the surface of the platform. A plurality of waveguides may be defined in a single trench on the substrate or each waveguide may have its own trench. In addition, many other fabrication processes, using different processing steps, materials or parameters, may be within the scope of the invention. The contemplated scope of the invention is defined in the claims which follow.

The invention claimed is:

1. A device comprising:
    a flexible substrate composed of a first polymer having one or more trenches defined therein;
    one or more optical waveguides disposed in the one or more trenches, the one or more optical waveguides composed of a second polymer;
    one or more pairs of out-of-plane input and output coupling mechanisms integrally formed in the flexible substrate to redirect a direction of travel of light in an out-of-plane direction;
    a light source integrated with the input coupling mechanism; and
    one or more metal traces disposed along a portion of a length of the device and separated from the one or more optical waveguides by a layer of the first polymer;
    wherein the first polymer has a lower refractive index than the second polymer; and
    wherein a reflective surface of each micromirror is a formed of a reflective metal.

2. The device of claim 1 wherein the first polymer is PDMS and the second polymer is Parylene C.

3. The device of claim 1 wherein the input coupling mechanism is an input micromirror disposed at one end of each optical waveguide and wherein the output coupling mechanism is an output micromirror disposed at an opposite end of each optical waveguide.

4. The device of claim 3 wherein each micromirror is angled at a 45° angle with respect to a longitudinal axis of each waveguide, such as to direct light transmitted through the waveguide in a direction perpendicular to the longitudinal axis of each waveguide.

5. The device of claim 3 wherein a reflective surface of each micromirror is composed of Aluminum.

6. The device of claim 2 wherein each waveguide is coated with a conformal coating of Parylene C.

7. The device of claim 2 wherein each waveguide is surrounded by a layer of PDMS cladding.

8. The device of claim 1 wherein the device is a neural probe.

9. A method of fabricating a photonic platform comprising:
    providing a substrate;
    defining one or more trenches in the substrate;
    depositing a sacrificial oxide layer covering the one or more trenches;
    depositing a first layer of a first polymer on the oxide layer;
    depositing a layer of a second polymer over the first polymer;

etching the layer of second polymer to define one or more optical waveguides in the one or more trenches;

depositing a layer of a reflective metal on an angled wall defined in the first layer of the first polymer at each end of each optical waveguide, forming input micromirrors at one end of each optical waveguides and output micromirrors at an opposite end of each optical waveguide;

depositing a second layer of the first polymer to cover the one or more waveguides;

bonding one or more vertical-cavity surface-emitting lasers to one or more of the input micromirrors using an anisotropic conductive film;

depositing one or more metal traces on the second layer of the first polymer; and releasing the photonic platform from the substrate.

10. The method of claim 9 wherein the first polymer is PDMS and the second polymer is Parylene C.

11. The method of claim 9 wherein the substrate is silicon.

12. The method of claim 9 further comprising:
depositing a conformal layer of the second polymer onto the one or more waveguides prior to depositing the layer of the second polymer to cover the one or more waveguides.

13. The method of claim 9 wherein defining one or more trenches in the substrate comprises:
coating the substrate with a thermal oxide layer;
etching the thermal oxide layer to form an etching mask on the substrate;
etching the one or more trenches in the surface of the substrate; and
removing the etching mask.

14. The method of claim 9 wherein releasing the photonic platform comprises:
removing the substrate by etching; and
removing the sacrificial oxide layer by etching.

15. The method of claim 9 wherein depositing a layer of a reflective metal comprises:
depositing a thin layer of Parylene C on the first layer or the first polymer;
depositing a layer of photoresist and patterning the location of the micromirrors in the photoresist;
depositing a layer of Platinum;
depositing layer of Aluminum over the layer of Platinum; and
removing the photoresist.

16. The method of claim 9 wherein depositing a layer of a reflective metal comprises:
depositing an adhesion layer;
depositing a layer of Platinum on the adhesion layer; and
depositing layer of Aluminum over the layer of Platinum.

17. The method of claim 9 wherein depositing a layer of a reflective metal comprises:
functionalizing the surface of the angled wall;
depositing a layer of Platinum on the angled wall; and
depositing layer of Aluminum over the layer of Platinum.

18. The method of claim 9 further comprising:
bonding an optical fiber to an input port of one or more of the waveguides using an optical epoxy.

19. The device of claim 3 wherein the light source is a vertical-cavity surface-emitting laser bonded to one or more of the input micromirrors using an anisotropic conductive film.

* * * * *